(12) United States Patent
Deng et al.

(10) Patent No.: US 8,017,784 B2
(45) Date of Patent: Sep. 13, 2011

(54) SUBSTITUTED SULFOXIDE COMPOUNDS, METHODS FOR PREPARING THE SAME AND USE THEREOF

(75) Inventors: Jingen Deng, Chengdu (CN); Qin Yang, Chengdu (CN); Yongle Chen, Zhuhai (CN); Jin Zhu, Chengdu (CN); Qiwei Wang, Chengdu (CN); Qiuya Huang, Chengdu (CN); Xuemei Hou, Zhuhai (CN)

(73) Assignee: Livzon Pharmaceutical Group, Inc., Zhuhai, Guangdong Province (CN)

( * ) Notice: Subject to any disclaimer, the term of this patent is extended or adjusted under 35 U.S.C. 154(b) by 652 days.

(21) Appl. No.: 12/126,355

(22) Filed: May 23, 2008

(65) Prior Publication Data

US 2008/0234487 A1 Sep. 25, 2008

Related U.S. Application Data

(63) Continuation of application No. 11/389,616, filed on Mar. 24, 2006, now abandoned.

(30) Foreign Application Priority Data

Mar. 25, 2005 (CN) .......................... 2005 1 0058962

(51) Int. Cl.
*C07D 401/14* (2006.01)
(52) U.S. Cl. .................................... 546/273.7
(58) Field of Classification Search ............... 546/273.7
See application file for complete search history.

(56) References Cited

U.S. PATENT DOCUMENTS

| | | | |
|---|---|---|---|
| 5,703,097 A * | 12/1997 | Kim et al. ..................... | 514/338 |
| 5,877,192 A | 3/1999 | Lindberg et al. | |
| 5,948,789 A | 9/1999 | Larsson et al. | |
| 6,894,066 B2 | 5/2005 | Sherman | |
| 2006/0217423 A1 | 9/2006 | Deng et al. | |

FOREIGN PATENT DOCUMENTS

WO  WO-9427988 A1  12/1994

OTHER PUBLICATIONS

Yang, "Preparation of sulfinyl, etc.," CA 140:357338, 2003.*
Wang et al., "Preparation of chiral, etc.," CA 140:181445, 2004.*
Jiang, "Preparation of, etc.," CA 141:140456, 2004.*
Cho et al. (2001), "Novel enantiomer of 5-pyrrolyl-2-pyridylmethylsulfinyl benzimidazole", Accession No. 2004:890375.
Guillory et al. (1999), "Generation of Polymorphs, Hydrates, Solvates, and Amorphous Solids", Brittain et al. ed., NY: Marcel Dekker, Inc., pp. 183-226.
Kil et al. (2001), "Comparison of IY81149 with omeprazole in rat reflux oesophagitis", J of Autonomic Pharmacology, 20:291-296.
Kim et al. (2001), "General pharmacology of IY-81149, a new proton pump inhibitor", Accession No. 2001:104664.
Vippagunta et al. (2001), "Crystalline solids", Advanced Drug Delivery Reviews, 48:3-26.

* cited by examiner

*Primary Examiner* — Patricia Morris
(74) *Attorney, Agent, or Firm* — Mintz Levin Cohn Ferris Glovsky and Popeo, P.C.; Ivor R. Elrifi

(57) ABSTRACT

Disclosed are an optically pure compound having formula I, its pharmaceutically acceptable salt and its pharmaceutically acceptable solvate, and a use thereof in manufacturing medicaments and pharmaceutical compositions. A process for preparing the compound defined therein is also provided.

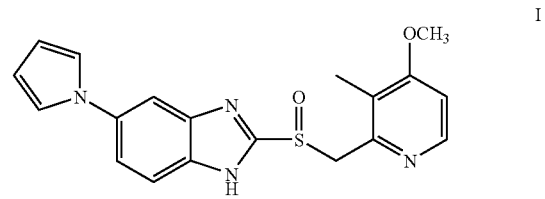

I

23 Claims, No Drawings

SUBSTITUTED SULFOXIDE COMPOUNDS, METHODS FOR PREPARING THE SAME AND USE THEREOF

CROSS REFERENCE OF RELATED APPLICATIONS

The present application is a continuation of U.S. application Ser. No. 11/389,616, filed on Mar. 24, 2006, abandoned, which claims the benefit of Chinese application No. 200510058962.3 filed on Mar. 25, 2005, entitled the same, the disclosures of which are hereby incorporated herein by reference in their entirety.

BACKGROUND OF THE INVENTION

1. Technical Field of the Invention

The present invention relates to substituted sulphoxides, particularly to optical isomers of "prazole" compounds. The present invention is also directed to a process for preparing optical isomers of "prazole" compounds, and use thereof in manufacturing medicaments.

2. Description of Prior Art

In general, peptic ulcer, of which 90% is gastric ulcer or duodenal ulcer, is caused by the enhancement of gastric mucosa injury factors, such as gastric acids, Helicobacter pylori (Hp), pepsins, non-steroidal anti-inflammatory drugs (NSAIDs) and the like, and/or the reduction of gastric mucosa defense factors, such as gastric mucosal barriers, mucosal blood flow, prostaglandin, reepithlialization, secretion of dicarbonates and the like, in body.

Generally, the immediate causes of ulcer include abnormal eating habit, excessive drinking, mental strain and various stresses, Hp infection, and administration of NSAIDs. Usually, Hp infection contributes to the onset, severity, progress, obstinateness and early relapse of ulcer, and gastric acid plays an important role in the injury of gastric mucosa and aggravation of ulcer. Therefore, "inhibition of gastric acid" and "eradication of Hp" (for Hp positive patients) have become two important aspects for current clinic treatment of peptic ulcer.

Many compounds having benzimidazole structures, such as Omeprazole, can inhibit any stimulated acid secretion from gastric parietal cell, i.e. inhibit the last step of the delivery of gastric acid from gastric parietal cell to gastral cavity, and therefore are very effective for treating ulcer. Since the last step involves in the exchange and transport of $H^+$ and $K^+$ induced by an enzyme, called $H^+$, $K^+$ transporting ATPase, this class of compounds that can inhibit the activity of $H^+$, $K^+$/ATPase are known as proton pump inhibitors (PPIs). Besides Omeprazole, such compounds are now commercially available with generic names of Lansoprazole, Pantoprazole, Rabeprazole, and Esomeprazole (an optically pure Omeprazole marketed in 2001).

"Prazoles" (i.e. PPIs) can be used alone to treat various peptic ulcer, including multiple ulcer caused by gastrin, drug-induced ulcer caused by NSAIDs, and $H_2$ receptor antagonist (such as Cimetidine and Ranitidine) resistant refractory ulcer. The recovery ratio of ulcer treated with "prazoles" is up to 80% in two weeks and up to 100% in four weeks, and the relapse ratio thereof is substantially reduced. For Hp positive patients, "prazoles" can be used in combination with two antibacterial agents, where PPIs can enhance the activity of the antibacterial agents, and as a result a clearance of over 90% of Hp may be achieved in two weeks. Currently, the triple therapeusis of PPIs and two antibacterial agents has become a primary treatment of Hp positive peptic ulcer.

Besides peptic ulcer, PPIs can also be used to treat gastro-oesophageal reflux diseases (GORD), zollinger-ellison syndrome (ZES) and other diseases associated with excessive gastric acid.

Il-Yang Pharm. Co., Ltd., Korea has developed a novel PPI, i.e. racemic 5-(1H-pyrrol-1-yl)-2-[[(3-methyl-4-methoxy-2-pyridyl)-methyl]sulfinyl]-benzimidazole, which shows superior anti-ulcer effects as compared with Omeprazole in the treatment of GORD, gastric ulcer and duodenal ulcer (KR 179,401 and U.S. Pat. No. 5,703,097).

The benzimidazoles described above as anti-ulcer agents are substituted sulphoxides having a stereogenic centre at the sulphur atom and thus exist as two optical isomers, i.e. enantiomers. If there is another stereogenic centre in the molecule, these compounds can exist as pairs of enantiomers. Corresponding sulphides of such compounds which already contain a stereogenic centre are not pro-chiral compounds, but chiral compounds. However, the sulphur atom in these compounds does not have asymmetry and therefore they are referred to as pro-chiral sulphides in respect of this invention. There are a large number of publications including patents and patent applications disclosing processes for preparation of the single enatiomers of such benzimidazole like Omeprazole, Lansoprazole, Pantoprazole and Rabeprazole, such as SE 9,500,818, DE 4,035,455, WO 94/27988 and ZL98124029.1 (which are hereby incorporated by reference in their entirety). It has been demonstrated that optically pure levo-Omeprazole (i.e. Esomeprazole) shows improved physiological activity and pharmacokinetics, and lower toxicity in comparison with the racemate of Omeprazole (Lindberg. P.; Weidolf, L. U.S. Pat. No. 5,877,192, 1999).

Our study on 5-(1H-pyrrol-1-yl)-2-[[(3-methyl4-methoxy-2-pyridyl)-methyl] sulfinyl]-benzimidazole has demonstrated that both its levo-enantiomer and dextro-enantiomer are inhibitors of gastric acid more potent than its racemate. However, the synthesis of such levo-enantiomer and dextro-enantiomer has never been reported in the art. Accordingly, we have made great efforts to study on the process for synthesis of the single enantiomers of 5-(1H-pyrrol-1-yl)-2-[[(3-methyl4-methoxy-2-pyridyl)-methyl]sulfinyl]-benzimidazole, and their use in medicaments for treatment of peptic ulcer and other diseases associated with excessive gastric acid.

Chinese patent CN 1070489C, which is hereby incorporated by reference herein in its entirety, has disclosed a process for enantioselective synthesis of Omeprazole, comprising asymmetrically oxidizing the corresponding prochiral sulphide in organic solvents (preferably toluene and ethyl acetate) in the presence of an organic base, a hydroperoxide, and a chiral titanium complex, which can be prepared from a titanium compound and a chiral alcohol. However, this process is not suitable for the synthesis of an enantiomerically enriched form of 5-(1H-pyrrol-1-yl)-2-[[(3-methyl4-methoxy-2-pyridyl) -methyl]sulfinyl]-benzimidazole due to its lower enantioselectivity and poor yield.

SUMMARY OF THE INVENTION

In a first aspect of the present invention, an optically pure compound of formula I,

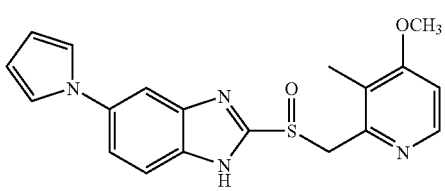

(IUPAC name: 5-(1H-pyrrol-1-yl)-2-[[(4-methoxy-3-methyl-2-pyridyl)-methyl]sulfinyl]-1-hydro-benzimidazole), a pharmaceutically acceptable salt thereof and a pharmaceutically acceptable solvate thereof are provided.

In a second aspect, the present invention relates to a use of an optically pure compound of formula I, its pharmaceutically acceptable salt, its pharmaceutically acceptable solvate or a mixture thereof in manufacturing medicaments or pharmaceutical compositions.

According to a preferred embodiment of the invention, the medicaments and pharmaceutical compositions are used for the treatment of a disease associated with excessive gastric acid, such as gastric ulcer, duodenal ulcer, GORD and Zollinger-Ellison syndrome.

In a third aspect, the present invention relates to a pharmaceutical composition comprising a therapeutically effective amount of an optically pure compound of formula I, its pharmaceutically acceptable salt, its pharmaceutically acceptable solvate or a mixture thereof, and a pharmaceutically acceptable carrier.

In a fourth aspect, the present invention relates to a method for treating a disease associated with excessive gastric acid, such as gastric ulcer, duodenal ulcer, GORD and Zollinger-Ellison syndrome, in a subject, comprising administering to the subject a therapeutically effective amount of an optically pure compound of formula I, its pharmaceutically acceptable salt, its pharmaceutically acceptable solvate or a mixture thereof.

In a fifth aspect, the present invention provides a process for preparing an optically pure compound of formula I, comprising oxidizing a pro-chiral sulphide of formula II in chloroform in the presence of an oxidant (as shown in Reaction 1).

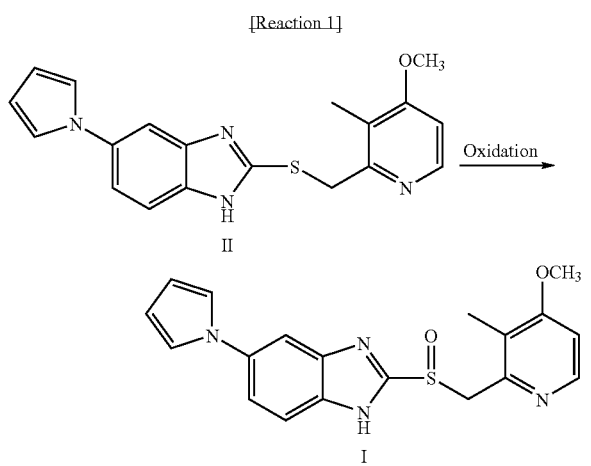

The process of the invention is characterized in that a pro-chiral sulphide is oxidized asymmetrically into a single enantiomer or an enantiomerically enriched form of the corresponding sulphoxide. And the process is more enantioselective in chloroform in comparison with processes using other solvents.

According to a particular embodiment of the invention, the process is carried out in the presence of a base and a chiral titanium complex using a hydroperoxide as the oxidant.

According to a preferred embodiment of the invention, a 4 Å molecular sieve is added to the reaction system, hereby increasing the yield of an optically pure compound of formula I. Preferably, the particle size of the 4 Å molecular sieve is about 4-8 mesh.

According to a further preferred embodiment of the invention, the process is carried out at a temperature ranging from room temperature to about 110° C., preferably from about 30° C. to about 80° C., and more preferably at about 31° C.

In a sixth aspect, the present invention relates to an intermediate compound having formula III, IUPAC name: 5-amino-2-[(4-methoxy-3-methyl-2-pyridyl)-methylthio]-1-hydro-benzimidazole.

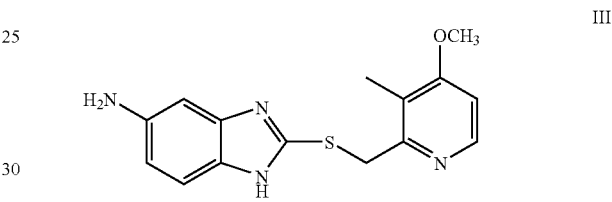

According to a preferred embodiment of the invention, the prochiral sulphide of formula II (IUPAC name: 5-(1H-pyrrol-1-yl)-2-[(4-methoxy-3-methyl-2-pyridyl)-methylthio]-1-hydro-benzimidazole) can be prepared by reacting the compound of formula III with a compound of formula IV in the presence of an acid (as shown in Reaction 2).

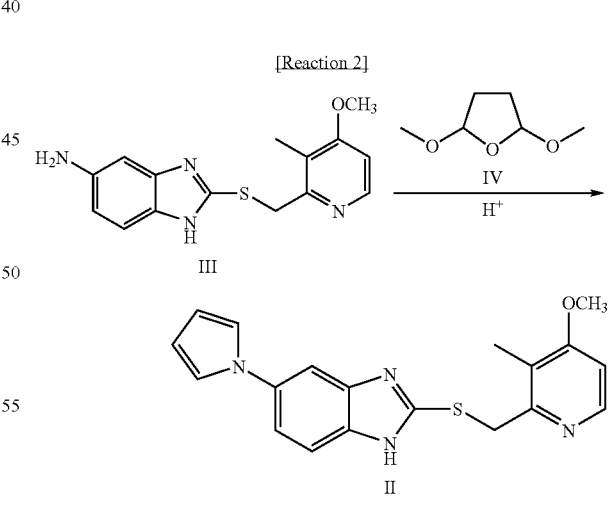

In a seventh aspect, the present invention relates to a process for preparing the intermediate of formula III, comprising reacting a compound of formula V with a compound of formula VI (as shown in Reaction 3).

[Reaction 3]

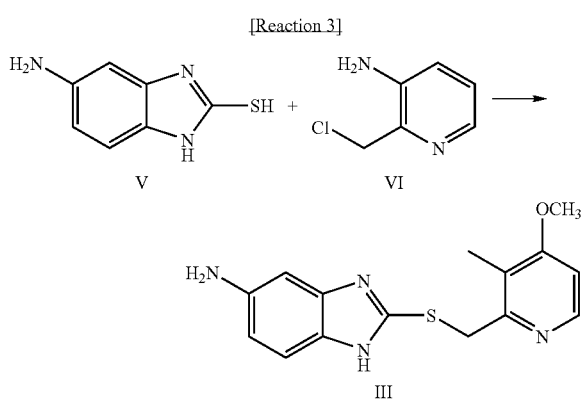

Tests carried out with animals have demonstrated that both the optically pure compounds of the present invention are more effective than their racemate in treating diseases associated with excessive gastric acid.

DETAILED DESCRIPTION OF THE INVENTION

One aspect of the present invention relates to an optically pure compound of formula I, its pharmaceutically acceptable salt and its pharmaceutically acceptable solvate, and a use thereof in manufacturing medicaments and pharmaceutical compositions.

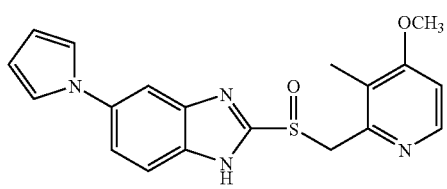

Unless specified otherwise, the expression "an (the) optically pure compound of formula I" or "an (the) active ingredient", as used herein, refers to (−)-5-(1H-pyrrol-1-yl)-2-[[(4-methoxy-3-methyl-2-pyridyl)-methyl]sulfinyl]-1-hydro-benzimidazole or (+)-5-(1H-pyrrol-1-yl)-2-[[(4-methoxy-3-methyl-2-pyridyl)-methyl]sulfinyl]-1-hydro-benzimidazole.

The term "pharmaceutically acceptable salt(s)", as used herein, refers to any pharmaceutically acceptable salt, which has desired pharmacological activities, of the compound according to the present invention. Such salts may include, but are not limited to, the following forms: (1) acid addition salts, wherever applicable, prepared by treatment with suitable acids such as inorganic and organic acids, of which examples of the inorganic acids include, but are not limited to, hydrohalic acid (such as hydrochloric acid, hydrobromic acid, hydrofluoric acid, and hydroiodic acid), sulfuric acid, nitric acid, phosphoric acid, perchloric acid, boric acid and the like; examples of the organic acids include, but are not limited to, tartaric acid, mandelic acid, fumaric acid, succinic acid, malic acid, salicylic acid, maleic acid, citric acid, palmitic acid, cinnamic acid, lactic acid, ascorbic acid, hydroxynaphthoic acid, gluconic acid, glutamic acid, acetic acid, propionic acid, propandioic acid, butanedioic acid, glycolic acid, keto-acetic acid, methane sulfonic acid, ethane sulfonic acid, benzene sulfonic acid, p-toluene sulfonic acid, cyclamic acid, 2-naphthalenesulfonic acid, camphorsulfonic acid, laurylsulfonic acid, benzoic acid, glycerophosphoric acid, ketoglutaric acid, stearic acid and other organic acids well-known in the art; or (2) salts, wherever applicable, prepared by substituting an acidic proton on the benzimidazole moiety of the compound with a metal atom (such as an alkali metal like Li, Na and K, an alkali earth metal like Mg and Ca, Zn or Al) or reacting with an organic base, such as ethanolamine, diethanolamine, triethanolamine and N-methyl glucamine.

The term "pharmaceutically acceptable solvate(s)" used herein means hydrates of a compound or compounds comprising other solvents of crystallization such as alcohols.

Another aspect of the present invention is directed to a pharmaceutical composition containing a therapeutically effective amount of an optically pure compound of formula I, its pharmaceutically acceptable salt, or its pharmaceutically acceptable solvate or a mixture thereof, and a pharmaceutically acceptable carrier.

In the present invention, when referring to a mixture of an optically pure compound of formula I and/or its pharmaceutically acceptable salt and/or its pharmaceutically acceptable solvate, the racemate of the compound of formula I, its pharmaceutically acceptable salt, its pharmaceutically acceptable solvate or a mixture thereof is excluded.

Carriers suitable for use in the present invention include pharmaceutically acceptable organic or inorganic carriers suitable for parenteral and intestinal (oral) administration, which have no adverse effect on the active ingredient. Suitable carriers include, but are not limited to, water, saline solution, alcohols, acacia, vegetable oils, benzalcohol, polyethylene glycol, gelatin, sugars (such as lactose), amylose or starch, magnesium stearate, talc, silicic acid, viscous paraffin, volatile oil, fatty acid monoglycerides and diglycerides, pentaerythritol fatty acid ester, carboxymethyl cellulose, polyvinylpyrrolidone, hydroxypropyl methyl cellulose, cellulose acetate Phthalate, Polyoxylate, Hypromellose Phthalate and the analogous compounds.

The concentration of the active compounds in the composition according to the present invention may vary depending on its absorption, distribution, metabolism and evacuating rate in vivo, as well as other factors known well in the art. It will be appreciated that the dose of the composition may vary according to the severity of conditions to be treated, and the dosage schemes may be modified with the process of time according to the estimations of the professionals for a specific subject.

The composition of the invention can be formulated into various pharmaceutically acceptable dosage forms, in which a suitable pharmaceutically acceptable carrier may be used. Such dosage forms include, but are not limited to capsules (including sustained-release or delayed-release dosage forms), tablets, powders, solutions, suspensions, syrups, pills, granula, elixirs, tinctures, implants (including suppository), emulsions, and injections, preferably gastro-resistant capsules or tablets.

For parenteral administration, the suitable dosage forms include injectable sterile solutions, lyophilized formulations, suspensions, emulsions and the like.

For intestinal administration, the suitable dosage forms include tablets, dragees, liquor, drops, capsules, syrups, tinctures and the like.

The preparations of the invention may be administered alone or in combination with other active agents such as antimicrobials.

Another aspect of the invention relates to a method for treatment of a disease associated with excessive gastric acid, such as gastric ulcer, duodenal ulcer, GORD and Zollinger-Ellison syndrome, in a subject, comprising administering to the subject a therapeutically effective amount of an optically pure compound of formula I, its pharmaceutically acceptable salt, its pharmaceutically acceptable solvate or a mixture thereof.

The term "subject", as used herein, refers to an animal, preferably a mammal, most preferably a human, who is the object of treatment, observation or experiment.

For treatment of any disease mentioned above, the optically pure compound of formula I may be administered, for example, orally or parenterally in an effective amount in a suitable formulation (optionally including various conventional pharmaceutically acceptable carriers). Furthermore, the optically pure compound of formula I may be administered alone or in combination with other active agents such as antimicrobials, in single or multiple doses.

Solid dosage forms for oral administration include tablets, pills, granules, capsules, and the like. The solid dosage forms may comprise any of the following components or any compound having similar properties: excipients such as microcrystalline cellulose, sodium citrate, calcium carbonate, dipotassium phosphate and glycine; disintegrants such as starch more preferably corn, potato or tapioca starch, alginic acid, sodium carbonate and certain complex silicates; binders like polyvinylpyrrolidone, sucrose, gelatin and acacia; humectants such as, for example, glycerol; solution retarding agents, such as, for example paraffin; absorption accelerators such as, for example, quartenary ammonium compounds; wetting agents like cetyl alcohol and glycerol monostearate; absorbents like kaolin and bentonite clay; and flavorings such as peppermint, methyl salicylate, and orange flavoring. Additionally, magnesium stearate, sodium lauryl sulfate, talc, calcium stearate, solid polyethylene glycols and mixtures thereof are often added as lubricating agents for tabletting purposes. Besides the components mentioned above, liquid carriers such as fatty acids can also be used in capsules. The solid dosage forms of tablets, dragees, capsules, pills, and the granules can be prepared with coatings and shells such as enteric coatings, release controlling coatings and other coatings which are well known in the field of pharmaceutical formulation art. In the case of capsules, tablets and pills, the dosage form may also comprise buffering agents. They may also be so formulated that they release the active ingredient(s) only or preferentially in a certain part of the intestinal tract, optionally in a delayed manner. The active compounds can also be in micro-encapsulated form using one or more of the excipients noted above.

Liquid dosage forms for oral administration include pharmaceutically acceptable emulsions, microemulsions, solutions, suspensions, syrups, and elixirs. The diluents may be selected from water, ethanol, propylene glycol, isopropyl alcohol, ethyl carbonate, ethyl acetate, benzyl alcohol, benzyl benzoate, 1,3-butylene glycol, dimethyl formamide, oils for e. g. cottonseed, groundnut, corn, germ, olive, castor, sesame oils and the like, glycerol, tetrahydrofurfuryl alcohol, polyethylene glycols and esters of fatty acids like sorbitan and various combination thereof. For such oral consumption it is desirable to combine the active ingredient with various sweetening or flavoring agents, coloring matter or dyes, if so desired.

The dosage forms for parenteral administration, such as solutions and suspensions, may contain any of the following components: diluents such as water for injection, saline, fixed oil, polyethylene glycol, glycerol, propanediol and other synthesized solvents; antimicrobials such as benzalcohol and methyl p-hydroxybenzoates; antioxidants such as ascorbic acid and sodium bisulfite; complexants such as EDTA; buffering agents such as acetates, citrate and phosphate; and tension adjusting agents such as sodium chloride and glucose. For intravenous administration, preferred carriers include saline, PBS, and auxiliaries including, but not limited to, alum, aluminium phosphate and other oil-or water-emulsion auxiliaries.

The suitable dose of the compound according to the present invention for human may vary depending on the body weight and gender of the subject in need of such treatment, the disease to be treated and its condition, and the route of administration. Typically, a preferred dose for prevention or treatment of gastric and duodenal ulcer in adult human patients is about 1-1,000 mg per day, more preferably 3-1,000 mg per day.

Another aspect of the invention relates to a process for preparing an optically pure compound of formula I, comprising oxidizing asymmetrically a pro-chiral sulphide of formula II, 5-(1H-pyrrol-1-yl)-2-[(4-methoxy-3-methyl-2-pyridyl)-methylthio]-1-hydro-benzimidazole, in chloroform in the presence of an oxidant.

[Reaction 1]

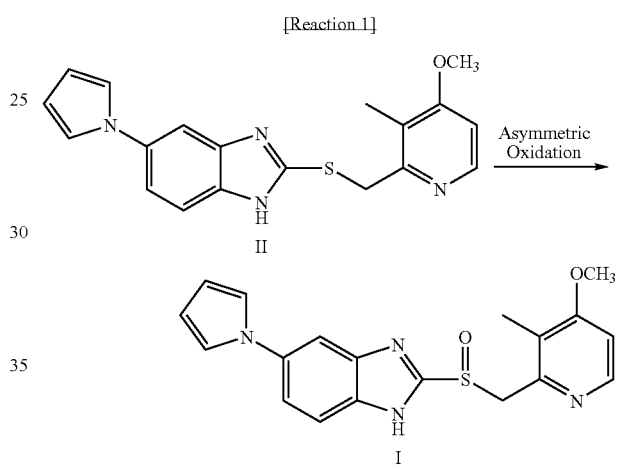

As described in CN1070489C, suitable solvents for use in the asymmetric oxidation of the sulphide of formula II may be selected from the group consisting of toluene, p-xylene, ethyl acetate, methyl ethyl ketone, methyl isobutyl ketone, diethyl carbonate, tert-butyl methyl ether, tetra-hydrofurane, methylene chloride and the like. However, it is surprisingly found that use of chloroform as a solvent has greatly improved the enantioselectivity of the asymmetric oxidation as compared with other solvents mention above.

In a preferred embodiment of the invention, a 4A molecular sieve is added to the reaction system, and as a result the yield of the enantiomerically enriched product can be improved. Preferably, the amount of the molecular sieve added is no more than about 10 times the weight of the substrates, more preferably about 1-5 times. A preferred particle size of the molecular sieve is around 4-8 mesh.

In a particular embodiment of the invention, the process of the invention is carried out in the presence of a base and a chiral titanium complex.

The base suitable for use in the process according to the present invention may be an inorganic base including but not limited to the hydroxides and dicarbonates of an alkali metal, or an organic base including but not limited to amides or amines which also include guanidines and amidines. Preferably, the base used is an organic base, more preferably an amine, and most preferably triethylamine or N,N-diisopropyl ethylamine. The amount of the base added may vary depending on the states of the reaction mixture, and preferably the amount is about 0.1-1.0 equivalents.

The titanium complex suitable for catalysing the process of the invention may be prepared from a chiral agent and a titanium compound, and optionally in the presence of water. A preferred titanium compound is titanium alkoxide, such as titanium iso-propoxide or -propoxide, and more preferably titanium tetraisopropoxide.

The chiral agent used in the preparation of the titanium complex is preferably a chiral alcohol such as a chiral diol. The diol may be a branched or linear alkyl diol, or an aromatic diol. Preferred chiral diols are esters of tartaric acid, and (+)-diethyl tartrate or (−)-diethyl tartrate are more preferred.

The amount of the chiral titanium complex is not critical. An amount used normally is not more than I equivalent, and a preferred amount is from about 0.05 to about I equivalent, and a more preferred amount is about 0.5 to 1 equivalent.

In a preferred embodiment, the chiral titanium complex may be activated in the presence of the pro-chiral sulphide of formula II. That is, the pro-chiral sulphide is added to the reaction vessel before the addition of the chiral titanium complex. Suitable temperature for the activation is in a range of from room temperature to about 115° C., and suitable activation time is about 1-10 hours.

In another preferred embodiment according to the present invention, the preparation and activation of the chiral titanium complex are simultaneously carried out in the presence of the pro-chiral sulphide of formula II, where the pro-chiral sulphide is added to the reaction vessel before the addition of components needed for preparing the chiral titanium complex. Suitable temperature for the preparation and activation ranges from room temperature to about 115° C., and suitable time is about 1-10 hours.

An oxidant suitable for the asymmetric oxidation may be a hydroperoxide, such as tert-butyl hydroperoxide or cumene hydroperoxide, preferably the latter. A preferred amount of the oxidant added is about 1-1.2 equivalents.

Typically, the oxidation is carried out at a temperature ranging from about −40° C. to about 115° C., preferably from room temperature to about 115° C., more preferably from 30° C. to about 80° C., most preferably at about 31° C.

In a preferred embodiment of the invention, after the oxidation, the resulted reaction mixture is extracted, dried and evaporated to afford a raw product, which is then purified by chromatography on silica gel using ethyl acetate as an eluant, yielding a product with an enantiomeric excess (ee) of 76-98%.

In a further preferred embodiment of the invention, the product of 76-98% ee is further recrystallized in an organic solvent selected from the group consisting of ethyl acetate, acetone, butanone, ethyl ether, tert-butyl methyl ether, methylene chloride, chloroform and a mixture thereof yielding a product with a higher enantiomeric excess up to 99% (ee).

According to still another aspect of the invention, a novel compound of formula III, 5-amino-2-[(4-methoxy-3-methyl-2-pyridyl)-methylthio]-1-hydro-benzimidazole, is provided, which can react with a compound of formula IV, 2,5-dimethoxy-tetrahydrofuran, in the presence of an acid to yield the sulphide of formula II (as shown in Reaction 2).

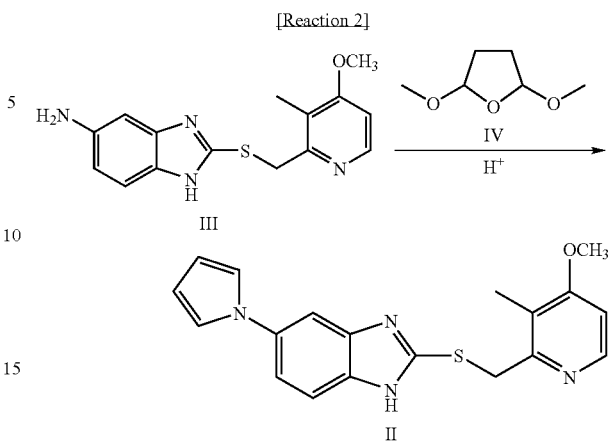

A preferred acid suitable for use in Reaction 2 is an organic acid, more preferably a glacial acetic acid. And the reaction is preferably carried out at a temperature of about 80°-150° C. or a refluxing temperature of the solvent used. The molar ratio of the compound of formula III to the compound of formula IV is preferably about 1:1.

In a preferred embodiment, the resulted mixture from the reaction was extracted, dried and evaporated to produce a raw product, which is then recrystallized in ethyl ether or methanol giving the compound of formula II.

In still another aspect, the invention relates to a process for preparing the compound of formula III comprising reacting a compound of formula V with a compound of formula VI in the presence of a solvent and a base (as shown in Reaction 3).

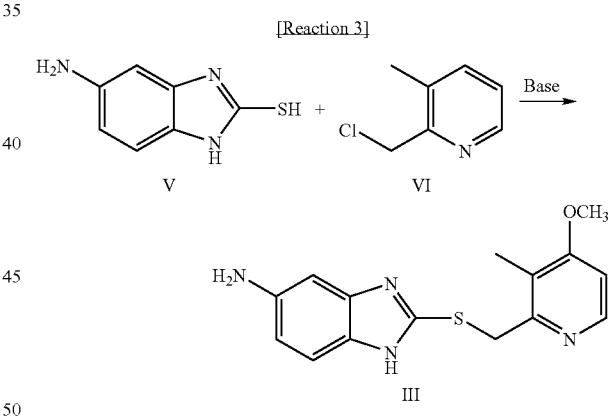

A preferred solvent suitable for use in Reaction 3 is a polar solvent, which is more preferably selected from the group consisting of methanol, ethanol, tetrahydrofuran, methylene chloride, cholorform, and a mixed solvent thereof with water. A base suitable for use in the reaction may be an organic base or an inorganic base, such as sodium hydroxide, potassium hydroxide, potassium carbonate, sodium methylate, sodium dicarbonate, sodium hydride, potassium hydride, pyridine, triethylamine, ethyl diisopropylamine and the like, and a mixture thereof. A preferred amount of the base added is about 1-2 equivalents, and a preferred temperature of the reaction is from about 0° C. to about 200° C. Preferably, the molar ratio of the compound of formula V to the compound of formula VI is about 1:1.

In a preferred embodiment, the resulted mixture from the reaction is filtered to remove solid precipitates, and the filtrate is evaporated under vacuum to yield a raw product of formula III, which can be directly used for preparing the compound of formula II without purification.

In a particular embodiment of the invention, the compound of formula V, 5-amino-2-mercapto-1-hydro-benzimidazole, may be prepared by reducing the compound of formula VII, 5-nitro-2-mercapto-1-hydro-benzimidazole, using conventional methods and under conditions well-known in the art (as shown in Reaction 4).

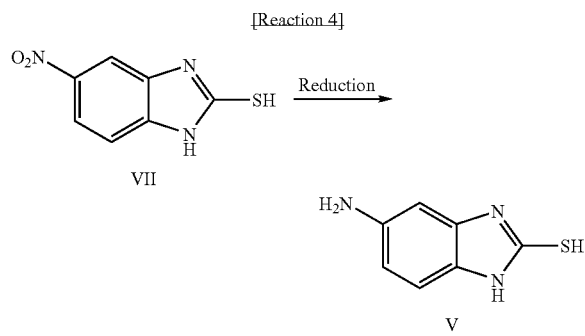

[Reaction 4]

In a preferred embodiment of the invention, the compound of formula VII is dissolved in methanol, ethanol, methylene chloride, chloroform or tetrahydrofuran, and 5-20 equivalents of zinc powder are then added in batches. To the mixture is added slowly a concentrated chlorhydric acid until the mixture turns colorless. After the reaction is completed, an insoluble precipitate is filtered off and the filtrate is adjusted to pH 9-10 by addition of a saturated solution of potassium carbonate. The mixture is decolored with activated carbon, heated to reflux for 0.5-2 hours, filtered with siliceous earth, and dried to afford the compound of formula V.

Hereinafter, the invention will be illustrated more in detail by the following examples for better understanding of various aspects and advantages of the invention. However, it should be understood that the examples below are non-limiting and are only illustrative of some of the embodiments of the present invention.

EXAMPLES

Preparations

Synthesis of 5-amino-2-mercapto-1-hydro-benzimidazole (V)

Method 1:

3 g (45.8 mmol) of zinc powder was added in batches into a stirred solution of 0.5 g (2.57 mmol) of 5-nitro-2-mercapto-1-hydro-benzimidazole (VII) in 50 mL methanol. 5 mL concentrated hydrochloric acid was then added dropwise to the mixture until it was decolored, and stirred for 0.5 hours at room temperature. After the reaction was completed, an insoluble material was filtered off, and 50 mL methanol was added to the filtrate which was adjusted to pH 9-10 by addition of a saturated solution of potassium carbonate. The reaction mixture was then heated to reflux for 0.5 hours, filtered, and evaporated to dry obtaining 0.27 g of the title compound as a yellow solid, yield 65.0%.

$^1$H-NMR(30 MHz, DMSO-d6): δ(ppm): 4.96(s, 2H), 6.37 (s, 1H), 6.39(d, J=9 Hz, 1H), 6.81(d, J=9 Hz, 1H).
Method 2:

16.8 g (257 mmol) of zinc powder was added in batches into a stirred solution of 5 g (25.7 mmol) 5-nitro-2-mercapto-1-hydro-benzimidazole (VII) in 300 mL absolute alcohol. 30 mL of concentrated hydrochloric acid was then added dropwise to the mixture until it was decolored, and stirred for 1 hour at room temperature. After the reaction was completed, an insoluble material was filtered off, and 100 mL ethanol was added to the filtrate which was adjusted to pH 9-10 by addition of a saturated solution of potassium carbonate. The reaction mixture was then heated to reflux for 1 hour, filtered, and evaporated to give 2.5 g the title compound as a yellow solid, yield 60.2%.
Method 3:

168 g (2.57 mol) of zinc powder was added in batches into a stirred solution of 50 g (257 mmol) of 5-nitro-2-mercapto-1-hydro-benzimidazole (VII) in 2,000 mL methanol. 320 mL concentrated hydrochloric acid was then added dropwise to the mixture until it was decolored, and stirred for 2 hours at room temperature. After the reaction was completed, an insoluble material was filtered off, and the filtrate was adjusted to pH9-10 by addition of a saturated solution of potassium carbonate. The reaction mixture was then heated to reflux for 1 hour, filtered, and evaporated to dry to afford 28 g of the title compound as a yellow solid, yield 67.4%.

Synthesis of 5-(1H-pyrrol-1-yl)-2-[(4-methoxy-3-methyl-2-pyridyl) -methylthio]-1-hydro-benzimidazole (II)

Method 1:

4.95 g (0.030 mol) 5-amino-2-mercapto-1-hydro-benzimidazole (V) and 2.88 g (0.072 mol) sodium hydroxide were dissolved in 30 mL water at room temperature, and 8.09 g (0.039 mol) 2-chloromethyl-3-methyl-4-methoxy-pyridine hydrochloride in 150 mL methanol was then added dropwise. After 3 hours, the reaction mixture was filtered and evaporated under vacuum to afford a raw product (III).

$^1$H-NMR(300 MHz, DMSO-d6): δ(ppm): 2.16(s, 3H), 3.84(s, 3H), 4.58(s, 2H), 6.43(d, J=7.8 Hz, 1H), 6.54(s, 1H), 6.93(d, J=5.7 Hz, 1H), 7.15(d, J=7.8 Hz, 1H), 8.23(d, J=5.7 Hz, 1H).

The raw product was dissolved in 60 mL acetic acid, and 4.65 mL (0.036 mol) 2,5-dimethoxy-tetrahydrofuran (IV) was then added with stirring, and the resultant was heated to reflux at 120° C. for 5 minutes. After the reaction was completed, the reaction mixture was poured into 200 mL water, and extracted with methylene chloride (100 mL×3). The combined organic phase was dried over anhydrous sodium sulfate, and evaporated under vacuum to remove the solvent. The residue was recrystallized in ethyl ether or methanol to afford 3.45 g of the title compound, yield 38.1%.

Melting point: 194.8-196.0° C.
$^1$H-NMR(300 MHz, CDCl$_3$): δ(ppm): 2.27(s, 3H), 3.91(s, 3H), 4.38(s, 2H), 6.34(t, J=2.1Hz, 2H), 6.78(d, J=6.0 Hz, 1H), 7.09(t, J=2.1Hz, 2H), 7.23-7.27(m, 1H), 7.53-7.56(m, 2H), 8.37(d, J=6.0 Hz, 1H).
Method 2:

29.7 g (0.18 mol) 5-amino-2-mercapto-1-hydro-benzimidazole (V) and 14.4 g (0.36 mol) sodium hydroxide were dissolved in a mixture of 200 mL water and 250 mL alcohol at room temperature, and 37.34 g (0.18mol) 2-chloromethyl-3-methyl-4-methoxy-pyridine hydrochloride in 200 mL ethanol was then added dropwise. After 3 hours, the reaction mixture was filter and evaporated under vacuum to afford a raw product (III). The raw product was dissolved in 300 mL acetic acid, and 27.9 mL (0.216 mol) 2,5-dimethoxy-tetrahydrofuran (IV) was added with stirring. The resultant was heated to reflux at 120° C. for 5 minutes. After the reaction was completed, the reaction mixture was poured into 1,000 mL water, and extracted with methylene chloride (500 mL×3). The combined organic phase was dried over anhydrous sodium sulfate, and evaporated under vacuum to remove the solvent. The residue was recrystallized in 30 mL methanol to afford 15.75 g of the title compound, yield 29%.
Asymmetric Synthesis (−)-5-(1H-pyrrol-1-yl)-2-[[(4-methoxy-3-methyl-2-pyridyl)-methyl]sulfinyl]-1-hydro-benzimidazole Example 1

49 μL (0.286 mmol) of (−)-diethyl tartrate and 43 μL (0.143 mmol) of titanium tetraisopropoxide were added to 50 mg (0.143 mmol) 5-(1H-pyrrol-1-yl)-2-[(4-methoxy-3-methyl-2-pyridyl)-methylthio]-1-hydro-benzimidazole (II) in 1 mL chloroform, and stirred for 5 minutes. To the solution was added 2.6 μL (0.143 mmol) of water. After stirring for 1 hour at room temperature, 25 μL (0.143 mmol) N,N-diisopropyl ethylamine and 31 μL (0.172 mmol) cumene hydroperoxide (80%) were successively added. The reaction was terminated after 18 hours at room temperature. Thereafter, the reaction mixture was extracted, dried and evaporated to afford a raw product, which was then purified by silica gel column chromatography eluting with ethyl acetate to give the title compound with an enantiomeric excess of 76.4% (identified by HPLC), yield 37.7%.

$^1$H-NMR(300 MHz, CDCl$_3$), δ(ppm): 2.21(s, 3H), 3.85(s, 3H), 4.72-4.91 (AB-system, J=13.5 Hz, 2H), 6.37(t, J=2.1Hz, 2H), 6.72(d, J=5.7 Hz, 1H), 7.10(t, J=2.1Hz, 2H), 7.38(d, J=8.7, 1H), 7.56(s, 1H), 7.66(d, J=8.7 Hz, 1H), 8.29(d, J=5.7 Hz, 1H).

HPLC conditions for determination of enantiomeric excess: Chiralpak OJ-H column, 35% isopropanol/n-hexane as eluent, flow rate 1 ml/min, wave length 254 nm, $RT_{(+)}$=9.588 min, $RT_{(−)}$=18.614 min.

Example 2

49 μL (0.286 mmol) (−)-diethyl tartrate and 43 μL (0.143 mmol) titanium tetraisopropoxide were added to 50 mg (0.143 mmol) 5-(1H-pyrrol-1-yl)-2-[(4-methoxy-3-methyl-2-pyridyl)-methylthio]-1-hydro-benzimidazole (II) in 1 mL chloroform at 31° C. After stirring for 1 hour at room temperature, 25 μL (0.143 mmol) N,N-diisopropyl ethylamine and 31 μL (0.172 mmol) cumene hydroperoxide (80%) were successively added. The reaction was terminated after 18 hours at 31° C. Thereafter, the reaction mixture was extracted, dried and evaporated to afford a raw product, which was then purified by silica gel column chromatography eluting with ethyl acetate to give the title compound with an enantiomeric excess of 88.0%, yield 49.7%.

Example 3

49 μL (0.286 mmol) (−)-diethyl tartrate and 43 μL (0.143 mmol) titanium tetraisopropoxide were added to 50 mg (0.143 mmol) 5-(1H-pyrrol-1-yl)-2-[(4-methoxy-3-methyl-2-pyridyl)-methylthio]-1-hydro-benzimidazole (II) in 1 mL chloroform at 31° C., and stirred for 5 minutes. To the solution was added 2.6 μL (0.143 mmol) of water. After stirring for 1 hour, 25 μL (0.143 mmol) N,N-diisopropyl ethylamine and 31 μL (0.172 mmol) cumene hydroperoxide (80%) were successively added. The reaction was terminated after 18 hours at 31° C. The reaction mixture was then extracted, dried and evaporated to afford a raw product, which was then purified by silica gel column chromatography eluting with ethyl acetate to give the title compound with an enantiomeric excess of 92.1%, yield 32.5%.

Example 4

49 μL (0.286 mmol) (−)-diethyl tartrate and 43 μL (0.143 mmol) titanium tetraisopropoxide were added to 50 mg (0.143 mmol) 5-(1H-pyrrol-1-yl)-2-[(4-methoxy-3-methyl-2-pyridyl)-methylthio]-1-hydro-benzimidazole (II) in 1 mL chloroform at 80° C., and stirred for 5 minutes. To the solution was added 2.6 μL (0.143 mmol) of water. After stirring for 1 hour, 25 μL (0.143 mmol) N,N-diisopropyl ethylamine and 31 μL (0.172 mmol) cumene hydroperoxide (80%) were successively added. The reaction was terminated after 18 hours at 80° C. The reaction mixture was then extracted, dried and evaporated to afford a raw product, which was then purified by silica gel column chromatography eluting with ethyl acetate to give the title compound with an enantiomeric excess of 93.7%, yield 24.7%.

Example 5

49 μL (0.286 mmol) (−)-diethyl tartrate and 43 μL (0.143 mmol) titanium tetraisopropoxide were added to 50 mg (0.143 mmol) 5-(1H-pyrrol-1-yl)-2-[(4-methoxy-3-methyl-2-pyridyl)-methylthio]-1-hydro-benzimidazole (II) in 1 mL chloroform, and stirred for 5 minutes. To the solution was added 2.6 μL (0.143 mmol) of water. After stirring for 1 hour at room temperature, 25 μL (0.143 mmol) N,N-diisopropyl ethylamine and 31 μL (0.172 mmol) cumene hydroperoxide (80%) were successively added. The reaction was terminated after 1 hour at 30° C. The reaction mixture was then extracted, dried and evaporated to afford a raw product, which was then purified by silica gel column chromatography eluting with ethyl acetate to give the title compound with an enantiomeric excess of 64.1%, yield 32.7%.

Example 6

100 mg 4 Å molecular sieve (4-8 mesh), 49 μL (0.286 mmol) (−)-diethyl tartrate and 43 μL (0.143 mmol) titanium tetraisopropoxide were added to 50 mg (0.143 mmol) 5-(1H-pyrrol-1-yl)-2-[(4-methoxy-3-methyl-2-pyridyl)-methylthio]-1-hydro-benzimidazole (II) in 1 mL chloroform at room temperature, and stirred for 5 minutes. To the solution was added 2.6 μL (0.143 mmol) of water. After stirring for 1 hour, 25 μL (0.143 mmol) N,N-diisopropyl ethylamine and 31 μL (0.172 mmol) cumene hydroperoxide (80%) were successively added. The reaction was terminated after 16 hours at room temperature. The reaction mixture was then extracted, dried and evaporated to afford a raw product, which was then purified by silica gel column chromatography eluting with ethyl acetate to give the title compound with an enantiomeric excess of 89.4%, yield 39.9%.

Example 7

100 mg 4 Å molecular sieve (4-8 mesh), 49 μL (0.286 mmol) (−)-diethyl tartrate and 43 μL (0.143 mmol) titanium tetraisopropoxide were added to 50 mg (0.143 mmol) 5-(1H-pyrrol-1-yl)-2-[(4-methoxy-3-methyl-2-pyridyl)-methylthio]-1-hydro-benzimidazole (II) in 1 mL chloroform at 31° C., and stirred for 5 minutes. To the solution was added 2.6 μL (0.143 mmol) of water. After stirring for 1 hour, 25 μL (0.143 mmol) N,N-diisopropyl ethylamine and 31 μL (0.172 mmol)

cumene hydroperoxide (80%) were successively added. The reaction was terminated after 18 hours at 31° C. The reaction mixture was then extracted, dried and evaporated to afford a raw product, which was then purified by silica gel column chromatography eluting with ethyl acetate to give the title compound with an enantiomeric excess of 92.8%, yield 76.5%.

Example 8

200 mg 4 Å molecular sieve (4-8 mesh), 49 µL (0.286 mmol) (−)-diethyl tartrate and 43 µL (0.143 mmol) titanium tetraisopropoxide were added to 50 mg (0.143 mmol) 5-(1H-pyrrol-1-yl)-2-[(4-methoxy-3-methyl-2-pyridyl)-methylthio]-1-hydro-benzimidazole (II) in 1 mL chloroform at 80° C., and stirred for 5 minutes. To the solution was added 2.6 µL (0.143 mmol) of water. After stirring for 1 hour, 25 µL (0.143 mmol) N,N-diisopropyl ethylamine and 31 µL (0.172 mmol) cumene hydroperoxide (80%) were successively added. The reaction was terminated after 18 hours at 80° C. The reaction mixture was then extracted, dried and evaporated to afford a raw product, which was then purified by silica gel column chromatography eluting with ethyl acetate to give the title compound with an enantiomeric excess of 96.2%, yield 35.5%.

Comparative Examples

In the following comparative examples, an enantiomerically enriched form of (−)-5-(1H-pyrrol-1-yl)-2-[[(4-methoxy-3-methyl-2-pyridyl)-methyl]sulfinyl]-1-hydro-benzimidazole was prepared according to the process disclosed in Chinese patent CN1070489C.

Comparative Example 1

19.6 µL (0.114 mmol) (−)-diethyl tartrate and 17.2 µL (0.057 mmol) titanium tetraisopropoxide were added to 20 mg (0.057 mmol) 5-(1H-pyrrol-1-yl)-2-[(4-methoxy-3-methyl-2-pyridyl)-methylthio]-1-hydro-benzimidazole (II) in 1 mL methylene chloride, and stirred for 5 minutes. To the solution was added 1.0 µL (0.057 mmol) of water. After stirring for 1 hour at room temperature, 10.0 µL (0.057 mmol) N,N-diisopropyl ethylamine and 12.4 µL (0.069 mmol) cumene hydroperoxide (80%) were successively added. The reaction was terminated after 22 hours at room temperature. The reaction mixture was then extracted, dried and evaporated to afford a raw product, which was purified by silica gel column chromatography eluting with ethyl acetate to give the title compound with an enantiomeric excess of 11.1%, yield 37.7%.

Comparative Example 2

19.6 µL (0.114 mmol) (−)-diethyl tartrate and 17.2 µL (0.057 mmol) titanium tetraisopropoxide were added to 20 mg (0.057 mmol) 5-(1H-pyrrol-1-yl)-2-[(4-methoxy-3-methyl-2-pyridyl)-methylthio]-1-hydro-benzimidazole (II) in 1 mL toluene, and stirred for 5 minutes. To the solution was added 1.0 µL (0.057 mmol) of water. After stirring for 1 hour at room temperature, 10.0 µL (0.057 mmol) N,N-diisopropyl ethylamine and 12.4 µL (0.069 mmol) cumene hydroperoxide (80%) were successively added. The reaction was terminated after 16 hours at room temperature. The reaction mixture was then extracted, dried and evaporated to afford a raw product, which was purified by silica gel column chromatography eluting with ethyl acetate to give the title compound with an enantiomeric excess of 23.3%, yield 5.2%.

Comparative Example 3

19.6 µL (0.114 mmol) (−)-diethyl tartrate and 17.2 µL (0.057 mmol) titanium tetraisopropoxide were added to 20 mg (0.057 mmol) 5-(1H-pyrrol-1-yl)-2-[(4-methoxy-3-methyl-2-pyridyl)-methylthio]-1-hydro-benzimidazole (II) in 1 mL toluene at 54° C., and stirred for 5 minutes. To the solution was added 1.0 µL (0.057 mmol) of water. After stirring for 1 hour at 54° C., 10.0 µL (0.057 mmol) N,N-diisopropyl ethylamine and 12.4 µL (0.069 mmol) cumene hydroperoxide (80%) were successively added. The reaction was terminated after 1 hour at 54° C. The reaction mixture was then extracted, dried and evaporated to afford a raw product, which was purified by silica gel column chromatography eluting with ethyl acetate to give the title compound with an enantiomeric excess of 36.5%, yield 33.3%.

Comparative Example 4

19.6 µL (0.114 mmol) (−)-diethyl tartrate and 17.2 µL (0.057 mmol) titanium tetraisopropoxide were added to 20 mg (0.057 mmol) 5-(1H-pyrrol-1-yl)-2-[(4-methoxy-3-methyl-2-pyridyl)-methylthio]-1-hydro-benzimidazole (II) in 1 mL toluene at 110° C., and stirred for 5 minutes. To the solution was added 1.0 µL (0.057 mmol) of water. After stirring for 1 hour at 110° C., 10.0 µL (0.057 mmol) N,N-diisopropyl ethylamine and 12.4 µL (0.069 mmol) cumene hydroperoxide (80%) were successively added. The reaction was terminated after 1 hour at 110° C. The reaction mixture was then extracted, dried and evaporated to afford a raw product, which was purified by silica gel column chromatography eluting with ethyl acetate to give the title compound with an enantiomeric excess of 53.1%, yield 35.4%.

Comparative Example 5

19.6 µL (0.114 mmol) (−)-diethyl tartrate and 17.2 µL (0.057 mmol) titanium tetraisopropoxide were added to 20 mg (0.057 mmol) 5-(1H-pyrrol-1-yl)-2-[(4-methoxy-3-methyl-2-pyridyl)-methylthio]-1-hydro-benzimidazole (II) in 1 mL toluene at 110° C., and stirred for 5 minutes. To the solution was added 1.0 µL (0.057 mmol) of water. After stirring for 1 hour at 110° C., 10.0 µL (0.057 mmol) N,N-diisopropyl ethylamine and 12.4 µL (0.069 mmol) cumene hydroperoxide (80%) were successively added. The reaction was terminated after 16 hours at 110° C. The reaction mixture was then extracted, dried and evaporated to afford a raw product, which was purified by silica gel column chromatography eluting with ethyl acetate to give the title compound with an enantiomeric excess of 29.2%, yield 21.4%.

Discussion

The condition, yield and enantiomeric excess of the examples and comparative examples are compared with each other as shown in Table 1.

TABLE 1

|  | Addition of water | Addition of molecule sieve | Solvents | Temperature (° C.) | Yield (%) | Enantiomeric Excess (%) |
|---|---|---|---|---|---|---|
| Examples |  |  |  |  |  |  |
| 1 | Yes | No | Chloroform | Room temperature | 37.7 | 76.4 |
| 2 | No | No | Chloroform | 31 | 49.7 | 88.0 |
| 3 | Yes | No | Chloroform | 31 | 32.5 | 92.1 |
| 4 | Yes | No | Chloroform | 80 | 24.7 | 93.7 |
| 5 | Yes | Yes | Toluene | 30 | 32.7 | 64.1 |
| 6 | Yes | Yes | Chloroform | Room temperature | 39.9 | 89.4 |
| 7 | Yes | Yes | Chloroform | 31 | 76.5 | 92.8 |
| 8 | Yes | Yes | Chloroform | 80 | 35.5 | 96.2 |
| Comparative Examples |  |  |  |  |  |  |
| 1 | Yes | No | Methylene Chloride | Room temperature | 37.7 | 11.1 |
| 2 | Yes | No | Toluene | 30 | 5.2 | 23.3 |
| 3 | Yes | No | Toluene | 54 | 33.3 | 36.5 |
| 4 | Yes | No | Toluene | 110 | 35.4 | 53.1 |
| 5 | Yes | No | Toluene | 110 | 21.4 | 29.2 |

From Table 1, it can be found that:

1. In cases that no 4 Å molecule sieve was added, the processes using methylene chloride or toluene as the solvent only achieved a lower enantiomeric excess (typically <55% ee), and in contrast the processes using chloroform as the solvent achieved a substantially higher enantiomeric excess (typically >75% ee).

2. In comparison with the cases without a 4 Å molecule sieve, the processes using a 4 Å molecule sieve achieved a higher yield, while keeping or improving their enantiomeric excess.

(+)-5-(1H-pyrrol-1-yl)-2-[[(4-methoxy-3-methyl-2-pyridyl)-methyl]sulfinyl]-1-hydro-benzimidazole Example 9

49 μL (0.286 mmol) (+)-diethyl tartrate and 43 μL (0.143 mmol) titanium tetraisopropoxide were added to 50 mg (0.143 mmol) 5-(1H-pyrrol-1-yl)-2-[(4-methoxy-3-methyl-2-pyridyl)-methylthio]-1-hydro-benzimidazole (II) in 1 mL chloroform at 31° C., and stirred for 5 minutes. To the solution was added 2.6 μL (0.143 mmol) of water. After stirring for 1 hour at 31° C., 25 μL (0.143 mmol) N,N-diisopropyl ethylamine and 31 μL (0.172 mmol) cumene hydroperoxide (80%) were successively added. The reaction was terminated after 18 hours at 31° C. The reaction mixture was then extracted, dried and evaporated to afford a raw product, which was purified by silica gel column chromatography eluting with ethyl acetate to give the title compound with an enantiomeric excess of 94.9% (determined by HPLC), yield 34.4%.

$^1$H-NMR(300 MHz, CDCl$_3$): δ(ppm): 2.21(s, 3H), 3.85(s, 3H), 4.72-4.91(AB-system, J=13.5 Hz, 2H), 6.37(t, J=2.1 Hz, 2H), 6.72(d, J=5.7 Hz, 1H), 7.10(t, J=2.1 Hz, 2H), 7.38(d, J=8.7, 1H), 7.56(s, 1H), 7.66(d, J=8.7 Hz, 1H), 8.29(d, J=5.7 Hz, 1H).

HPLC conditions for identification of enantiomeric excess: Chiralpak OJ-H column, 35% isopropanol/n-hexane as eluent, flow rate 1 ml/min, wave length 254 nm, RT$_{(+)}$=9.588 min, RT$_{(-)}$=18.614 min.

Example 10

100 mg, 4 Å molecular sieve (4-8 mesh), 49 μL (0.286 mmol) (+)-diethyl tartrate and 43 μL (0.143 mmol) titanium tetraisopropoxide were added to 50 mg (0.143 mmol) 5-(1H-pyrrol-1-yl)-2-[(4-methoxy-3-methyl-2-pyridyl)-methylthio]-1-hydro-benzimidazole (II) in 1 mL chloroform at 31° C. After stirring for 1 hour, 25 μL (0.143 mmol) N,N-diisopropyl ethylamine and 31 μL (0.172 mmol) cumene hydroperoxide (80%) were successively added. The reaction was terminated after 18 hours at 31° C. The reaction mixture was then extracted, dried and evaporated to afford a raw product, which was then purified by silica gel column chromatography eluting with ethyl acetate to give the title compound with an enantiomeric excess of 92.6%, yield 40.2%.

Purification of Asymmetrically Synthesized Product

Purification of (−)-5-(1H-pyrrol-1-yl)-2-[[(4-methoxy-3-methyl-2-pyridyl)-methyl]sulfinyl]-1-hydro-benzimidazole Method 1:

100 mg of (−)-5-(1H-pyrrol-1-yl)-2-[[(4-methoxy-3-methyl-2-pyridyl)-methyl]sulfinyl]-1-hydro-benzimidazole (90.2% ee) was dissolved in 0.5 mL methylene chloride with stirring at room temperature, and decolored with activated carbon. After filtration, 1.5 mL ethyl ether was added to the filtrate. The mixture was stirred for half an hour at room temperature, kept in a refrigerator over night, and then filtered to afford 42 mg of the titled compound as a white solid with an enantiomeric excess of 93.2%, yield 42%.

Method 2:

100 mg of (−)-5-(1H-pyrrol-1-yl)-2-[[(4-methoxy-3-methyl-2-pyridyl)-methyl]sulfinyl]-1-hydro-benzimidazole (90.2% ee) was dissolved in 10 mL acetone leaving a little solid undissolved. After filtration, the filtrate was decolored with activated carbon at room temperature, filtered and then evaporated. The residue was dissolved in 2 mL acetone, and the solution was stirred for half an hour at room temperature, kept in a refrigerator over night, and then filtered to afford 36 mg of the titled compound as a white solid with an enantiomeric excess of 93.7%, yield 36%.

Method 3:

100 mg of (−)-5-(1H-pyrrol-1-yl)-2-[ [(4-methoxy-3-methyl-2-pyridyl)-methyl] sulfinyl]-1-hydro-benzimidazole (87.3% ee) was dissolved in 10 mL acetone leaving a large amount of solid undissolved. After filtration, the filtrate was decolored with activated carbon at room temperature, filtered and then evaporated. The residue was dissolved in a mixture of 2 mL acetone and 4 mL ethyl acetate, and the solution was stirred for one day at room temperature, kept in a refrigerator over night, and then filtered to afford 32 mg of the titled compound as a light yellow solid with an enantiomeric excess of 96.2%, yield 32%.

Method 4:

20 mg of (−)-5-(1H-pyrrol-1-yl)-2-[[(4-methoxy-3-methyl-2-pyridyl)-methyl]sulfinyl]-1-hydro-benzimidazole (96.2% ee) was dissolved in 0.2 mL methylene chloride with stirring at room temperature to form a clear solution. The solution was decolored with activated carbon and filtered. 1.0 mL ethyl ether was added to the filtrate, and the solution was stirred for half an hour at room temperature, kept in a refrigerator over night, and then filtered to afford 12 mg of the titled compound as a white solid with an enantiomeric excess of over 99%, yield 60%.

$[\alpha]^D_{23} = -207.8$ (c=1, pyridine).

Purification of (+)-5-(1H-pyrrol-1-yl)-2-[[(4-methoxy-3-methyl-2-pyridyl)-methyl]sulfinyl]-1-hydro-benzimidazole Method 1:

100 mg of (+)-5-(1H-pyrrol-1-yl)-2-[[(4-methoxy-3-methyl-2-pyridyl)-methyl]sulfinyl]-1-hydro-benzimidazole (87.3% ee) was dissolved in 10 mL methylene chloride to form a clear solution. The solution was decolored with activated carbon at room temperature, filtered and then evaporated. The residue was dissolved in a mixture of 2 mL methylene chloride and 4 mL butanone, and the solution was stirred for two days at room temperature, kept in a refrigerator over night, and then filtered to afford 35 mg of the titled compound as a white solid with an enantiomeric excess of 96.8%, yield 35%.

Melting point: 167.1-167.3° C.

Method 2:

100 mg of (+)-5-(1H-pyrrol-1-yl)-2-[[(4-methoxy-3-methyl-2-pyridyl)-methyl]sulfinyl]-1-hydro-benzimidazole (87.3% ee) was dissolved in 10 mL acetone leaving a large amount of solid undissolved. The solution turned clear upon addition of 2 mL aqueous methylamine solution. The solution was decolored with activated carbon at room temperature, filtered and then evaporated. The residue was dissolved in a mixture of 2 mL acetone and 4 mL butanone, and the solution was stirred at room temperature for one day, kept in a refrigerator over night, and then filtered to afford 43 mg of the titled compound as a white solid with an enantiomeric excess of 97.7%, yield 43%.

$[\alpha]^D_{23} = +207.6$ (c=1, pyridine).

Method 3:

100 mg (+)-5-(1H-pyrrol-1-yl)-2-[[(4-methoxy-3-methyl-2-pyridyl)-methyl]sulfinyl]-1-hydro-benzimidazole (98.3% ee) was dissolved in 10 mL acetone leaving a large amount of solid undissolved. The solution turned clear upon addition of 2 mL aqueous methylamine solution. The solution was decolored with activated carbon at room temperature, filtered and then evaporated. The residue was dissolved in a mixture of 2 mL acetone and 4 mL butanone, and the solution was stirred for one day at room temperature, kept in a refrigerator over night, and then filtered to afford 51 mg of the titled compound as a white solid with an enantiomeric excess of over 99%, yield 51%.

PHARMACOLOGICAL TEST

Effect on Acute Gastric Ulcer of Rats (Pyloric Ligation Method)

Methodology

The effect of optically pure (+)/(−)-5-(1H-pyrrol-1-yl)-2-[[(4-methoxy-3-methyl-2-pyridyl)-methyl]sulfinyl]-1-hydro-benzimidazole on the acute gastric ulcer of rats were investigated using a pyloric ligation method (Shay method), and the results were compared with a normal control group and a racemate group. The specific test methods were as follows.

Twenty-six healthy SD female adult rats were divided randomly into 4 groups and fasted, except water, for 24 hours. Each rat was then anesthesized with 30 mg/kg Sodium Pentobarbital and subjected to pyloric ligation. After that, 3 groups of rats (treated group) were administered immediately via dodecadactylon with a racemate, a levo-enantiomer and a dextro-enantiomer of 5-(1H-pyrrol-1-yl)-2-[[(4-methoxy-3-methyl-2-pyridyl)-methyl]sulfinyl]-1-hydro-benzimidazole, respectively, at a dose of 3 mg/kg, and the other group (control group) is administered with the same volume of solvent.

All rats were then fasted including water for 6 hours followed by being sacrificed. The stomach was removed from rats after cardiac orifice ligation, and the volume of gastric juice was collected. After being fixed with 10% formalin solution, the stomach was incised along the greater curvature of stomach, the gastric wall was unwraped, and the degree and number of ulcers of the gastric mucosa were observed visually. Sum of the long diameter of each ulcer was defined as the index of ulcer. All rats were housed in metabolic cages during the test.

Results

The results were shown in Table 2.

TABLE 2

Effect on Acute Gastric Ulcer of Rats

| | Number of Rats | Dose (mg/kg) | Average Volume of Gastric Juice (ml), (Inhibition Ratio %) | Index of Ulcer (mm), (Inhibition Ratio %) |
|---|---|---|---|---|
| Control group | 8 | — | 4.6 ± 2.6 | 25 ± 16 |
| Racemate | 6 | 3 | 3.2 ± 2.3 (30.8%) | 14 ± 8 (41.8%) |
| Levo-enantiomer | 4** | 3 | 1.4 ± 1.0 (68.3%) | 6 ± 6* (75.6%) |
| Dextro-enantiomer | 6 | 3 | 2.6 ± 1.1 (43.2%) | 6 ± 7* (75.6%) |

Notes:
1. *compared with the control group, P < 0.05 using t-test.
2. **six rates were initially tested in this group, but one rat died during the test and one rat presented abnormal data which were excluded in view of statistics.
3. Inhibition ratio of gastric juice (%) =

$$\frac{\text{Average volume of gastric juice of control group} - \text{average volume of gastric juice of treated group}}{\text{Average volume of gastric juice of control group}} \times 100\%$$

TABLE 2-continued

Effect on Acute Gastric Ulcer of Rats

| Number of Rats | Dose (mg/kg) | Average Volume of Gastric Juice (ml), (Inhibition Ratio %) | Index of Ulcer (mm), (Inhibition Ratio %) |
|---|---|---|---|

4. Inhibition ratio of index of ulcer (%) =

$$\frac{\text{Average index of ulcer of control group} - \text{average index of ulcer of treated group}}{\text{Average index of ulcer of control group}} \times 100\%$$

From Table 2, the pilot study suggested that (1) after pyloric ligation, the rats of the control group showed clear evidences of acute gastric ulcer, such as increased gastric juice secretion and appearance of ulcer of the gastric mucosa; (2) as compared with the control group, the volume of gastric juice was reduced and the ulcer of the gastric mucosa was alleviated in all treated groups; and (3) both the levo-enantiomer and dextro-enantiomer of 5-(1H-pyrrol-1-yl)-2-[[(4-methoxy-3-methyl-2-pyridyl)-methyl]sulfinyl]-1-hydrobenzimidazole were more effective in inhibiting gastric juice secretion and ulceration as compared with their racemate.

It should be understood that although the present invention has been specifically disclosed by preferred embodiments and optional features, modification and variation of the concepts herein disclosed may be resorted to by those skilled in the art, and that such modifications and variations are considered to be falling within the scope of the invention.

The invention claimed is:

1. A process for preparing an optically pure compound of formula I with an enantiomeric excess (ee) of greater than 64.1%, comprising oxidizing asymmetrically a pro-chiral sulphide of formula II and adding a 4 Å molecular sieve to the reaction system, in chloroform in the presence of an oxidant, wherein the oxidation reaction is carried out as follows:

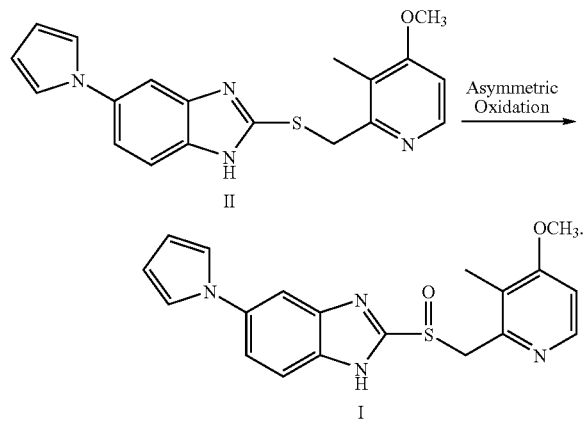

2. The process of claim 1, wherein the ee of compound of formula I is between 76-98%.

3. The process of claim 1, wherein the amount of molecular sieve added is no more than 10 times the weight of the substrates.

4. The process of claim 1, wherein the particle size of the molecular sieve is 4-8 mesh.

5. The process of claim 1, wherein the process is carried out in the presence of a base and a chiral titanium complex.

6. The process of claim 5, wherein the base is selected from amides, amines, guanidines and amidines.

7. The process of claim 6, wherein the base is triethylamine or N, N diisopropyl ethylamine.

8. The process of claim 5, wherein the titanium complex is prepared from a chiral agent and a titanium compound.

9. The process of claim 8, wherein the chiral agent is selected from branched alkyl diol, linear alkyl diol and aromatic diol.

10. The process of claim 8, wherein the chiral agent is (+)-diethyl tartrate or (−)-diethyl tartrate.

11. The process of claim 8, wherein the titanium compound is titanium alkoxide.

12. The process of claim 11, wherein the titanium compound is titanium tetraisopropoxide.

13. The process of claim 5, wherein the amount of chiral titanium complex is 0.05-1 equivalent.

14. The process of claim 1, wherein the process is carried out at a temperature from room temperature to about 115° C.

15. The process of claim 14, wherein the process is carried out at a temperature from about 30° C. to about 80° C.

16. The process of claim 15, wherein the process is carried out at a temperature about 31° C.

17. The process of claim 1, wherein the reaction time is about 1-10 hours.

18. The process of claim 1, wherein the oxidant is a hydroperoxide.

19. The process of claim 18, wherein the oxidant is tert-butyl hydroperoxide or cumene hydroperoxide.

20. The process of claim 1, wherein the amount of the oxidant added is about 1-1.2 equivalents.

21. The process of claim 1, further comprising the step of purifying the reaction product by chromatography on silica gel using ethyl acetate as an eluant.

22. The process of claim 1, further comprising the step of recrystallizing the product in an organic solvent selected from ethyl acetate, acetone, butanone, ethyl ether, tert-butyl methyl ether, methylene chloride, chloroform and a mixture thereof.

23. The process of claim 3, wherein the amount of the molecular sieve added is no more than 1-5 times the weight of the substrates.

* * * * *